(12) United States Patent
Pixner

(10) Patent No.: US 10,667,965 B2
(45) Date of Patent: Jun. 2, 2020

(54) MEDICAL FILE AND FIRST AID ASSEMBLY

(71) Applicant: Greg Pixner, Kitchener (CA)

(72) Inventor: Greg Pixner, Kitchener (CA)

( * ) Notice: Subject to any disclaimer, the term of this patent is extended or adjusted under 35 U.S.C. 154(b) by 0 days.

(21) Appl. No.: 16/057,054

(22) Filed: Aug. 7, 2018

(65) Prior Publication Data
US 2020/0046581 A1 Feb. 13, 2020

(51) Int. Cl.
*A45C 5/06* (2006.01)
*A61F 17/00* (2006.01)
*B42F 7/08* (2006.01)
*A45C 13/02* (2006.01)

(52) U.S. Cl.
CPC ............... *A61F 17/00* (2013.01); *A45C 5/06* (2013.01); *A45C 13/02* (2013.01); *B42F 7/08* (2013.01)

(58) Field of Classification Search
CPC ... A45C 5/06; A45C 13/02; B42F 7/08; A61F 17/00
USPC .......................................... 206/570; 190/111
See application file for complete search history.

(56) References Cited

U.S. PATENT DOCUMENTS

| | | | | |
|---|---|---|---|---|
| 2,487,220 A * | 11/1949 | Callaghan | ................ | A45C 3/06 206/541 |
| 5,207,303 A | 5/1993 | Oswall | | |
| 6,502,742 B1 * | 1/2003 | Su | ............... | B42F 7/08 229/67.3 |
| 6,575,273 B1 * | 6/2003 | Bergkvist | ................ | A45C 3/00 190/114 |
| 6,945,399 B1 * | 9/2005 | Ong | ......... | A45C 3/02 206/425 |
| 6,957,738 B2 | 10/2005 | Hammond | | |
| 7,467,695 B2 * | 12/2008 | Gormick | .................. | A45C 3/02 190/102 |
| D658,361 S | 5/2012 | Kontos | | |
| 9,027,721 B1 | 5/2015 | Osborne | | |
| 2006/0289329 A1 | 12/2006 | Miller | | |
| 2007/0131577 A1 | 6/2007 | Call | | |
| 2007/0228097 A1 * | 10/2007 | Recanati | ................ | A45C 13/02 224/580 |
| 2010/0307649 A1 | 12/2010 | Santos Dominguez | | |
| 2014/0358130 A1 * | 12/2014 | Gardner | ................ | A61B 50/20 606/1 |
| 2015/0027918 A1 * | 1/2015 | Chaturvedi | ............... | A61J 1/10 206/459.1 |

* cited by examiner

*Primary Examiner* — King M Chu

(57) ABSTRACT

A medical file and first aid assembly for storing medical files along with first aid supplies includes a storage case that is carried by a trainer of a sports team. The storage case has a plurality of trays that is pivotally positioned therein for storing first aid supplies. A file accordion is movably coupled to the storage case for storing medical history of each player on the sports team. In this way the trainer has access to medical history of each player for safely applying first aid to each player. A communication unit is coupled to the storage case and the communication unit is in electrical communication with an extrinsic communication network thereby facilitating inventory of the first aid supplies to be tracked and remotely ordered for re-supply.

7 Claims, 6 Drawing Sheets

MEDICAL FILE AND FIRST AID ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to first aid devices and more particularly pertains to a new first aid device for storing medical files along with first aid supplies.

BRIEF SUMMARY OF THE INVENTION

An embodiment of the disclosure meets the needs presented above by generally comprising a storage case that is carried by a trainer of a sports team. The storage case has a plurality of trays that is pivotally positioned therein for storing first aid supplies. A file accordion is movably coupled to the storage case for storing medical history of each player on the sports team. In this way the trainer has access to medical history of each player for safely applying first aid to each player. A communication unit is coupled to the storage case and the communication unit is in electrical communication with an extrinsic communication network thereby facilitating inventory of the first aid supplies to be tracked and remotely ordered for re-supply.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
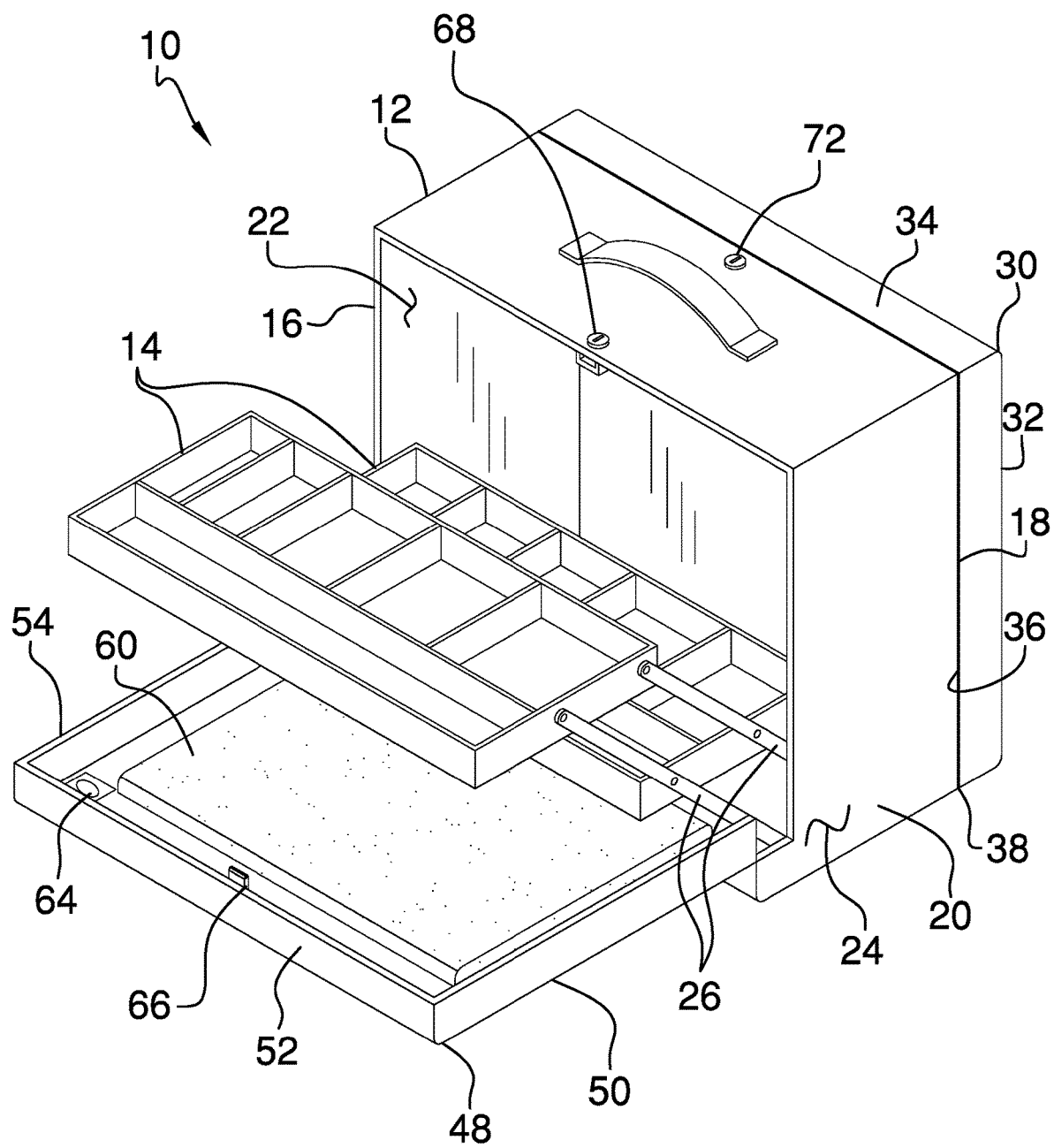
FIG. 1 is a front perspective view of a medical file and first aid assembly according to an embodiment of the disclosure.
Figure 2:
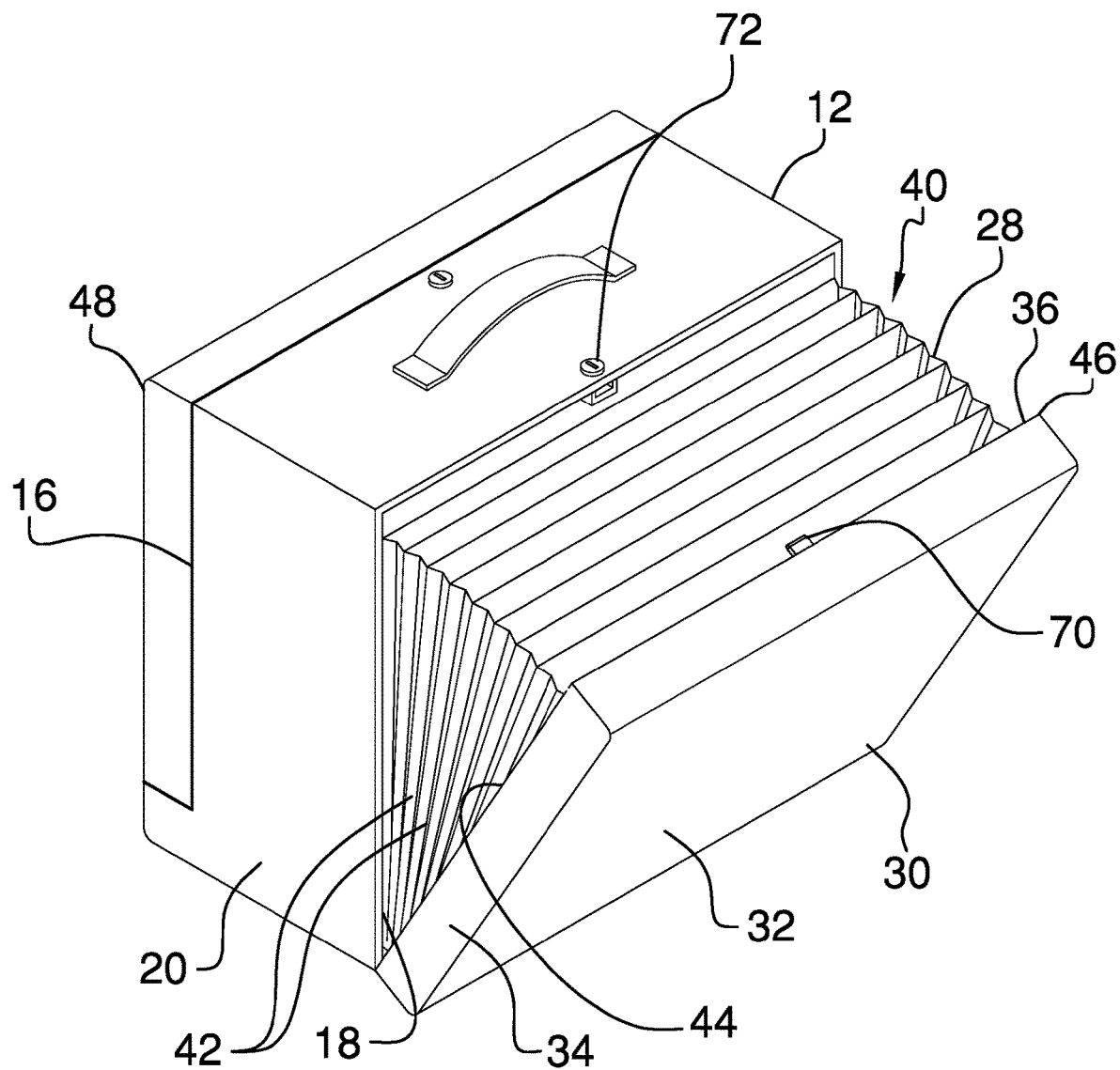
FIG. 2 is a top perspective view of an embodiment of the disclosure.
Figure 3:
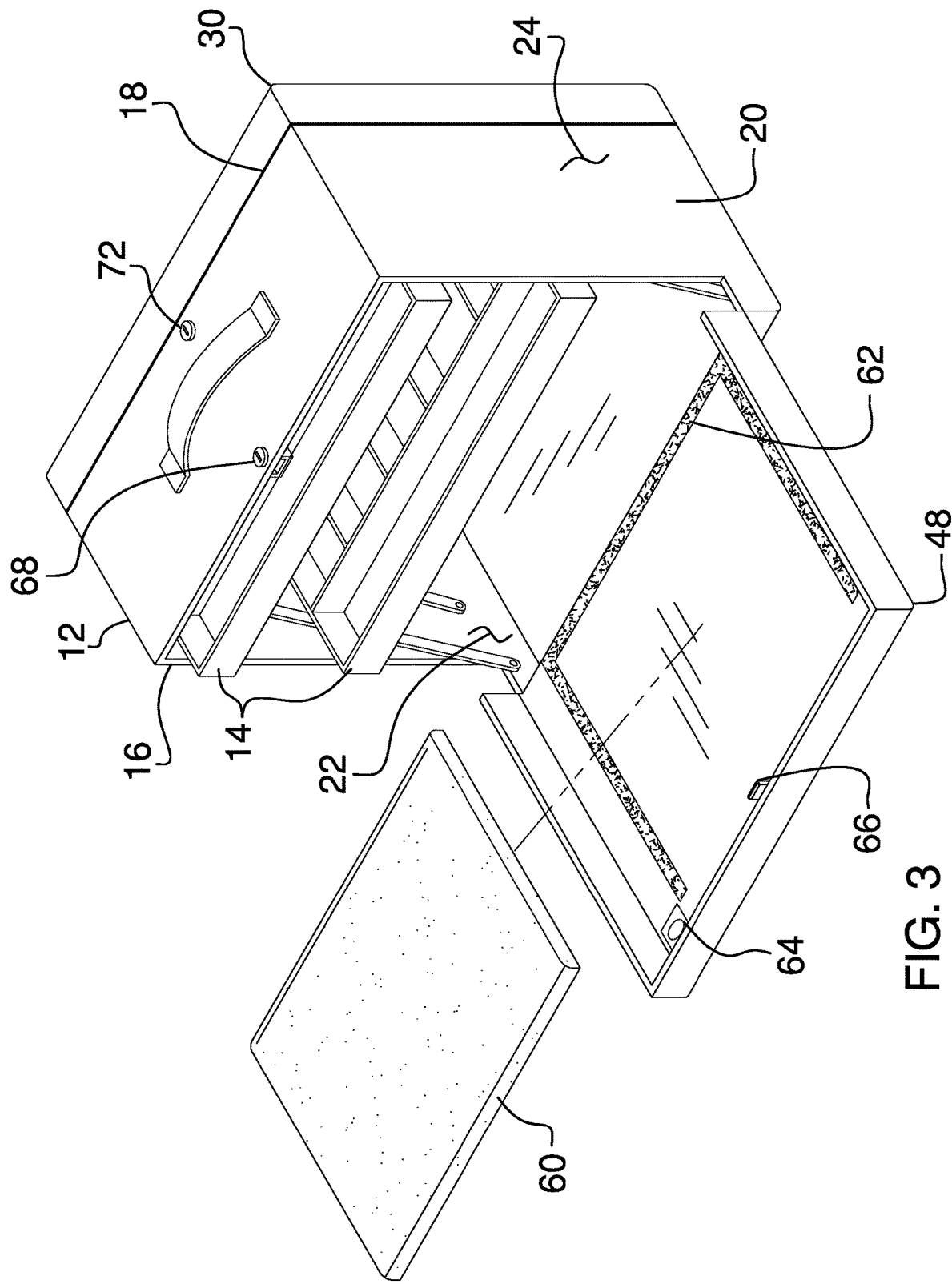
FIG. 3 is a front exploded view of an embodiment of the disclosure.
Figure 4:
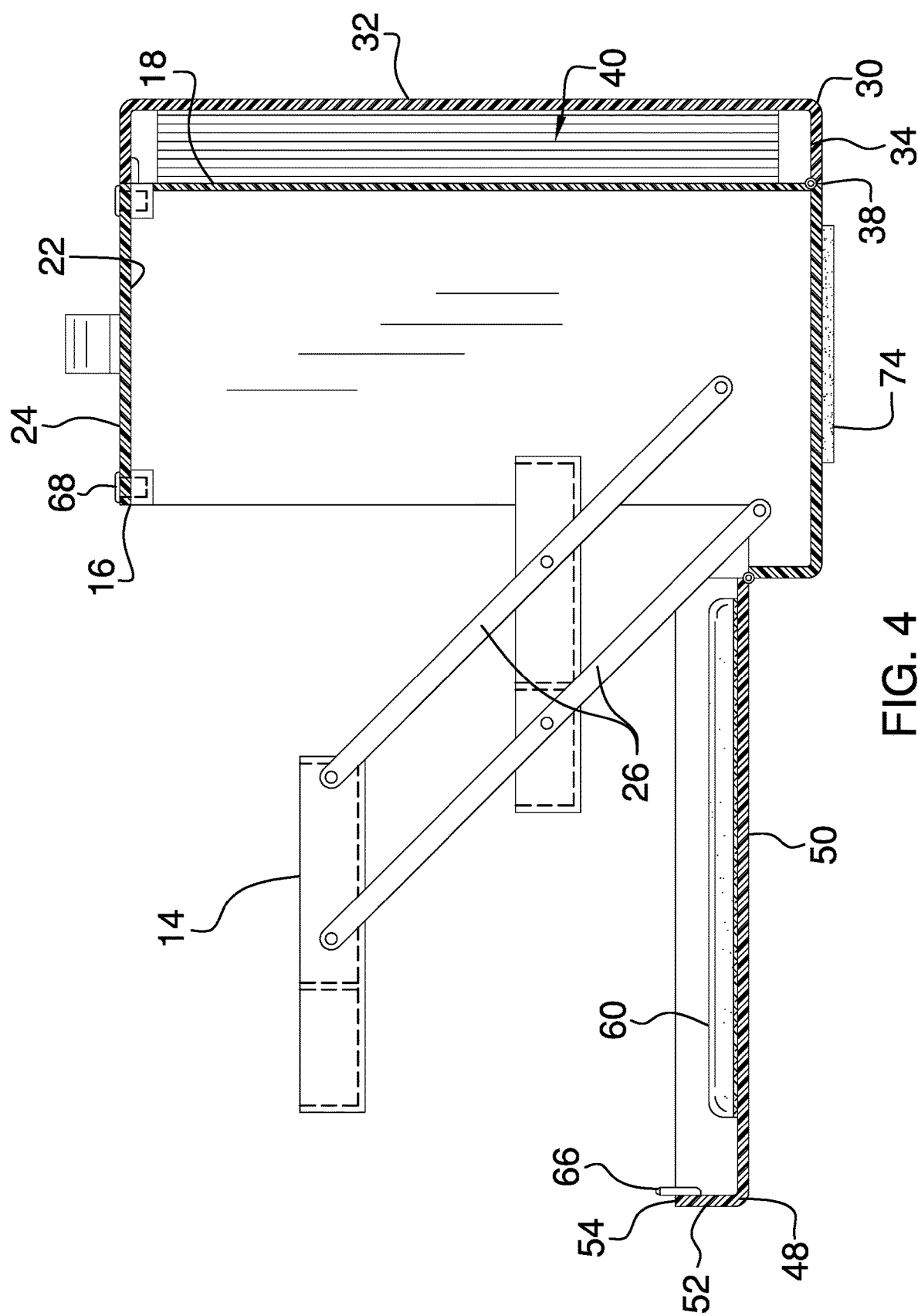
FIG. 4 is a right side cut-away view of an embodiment of the disclosure showing trays being extended outwardly from a storage case.
Figure 5:
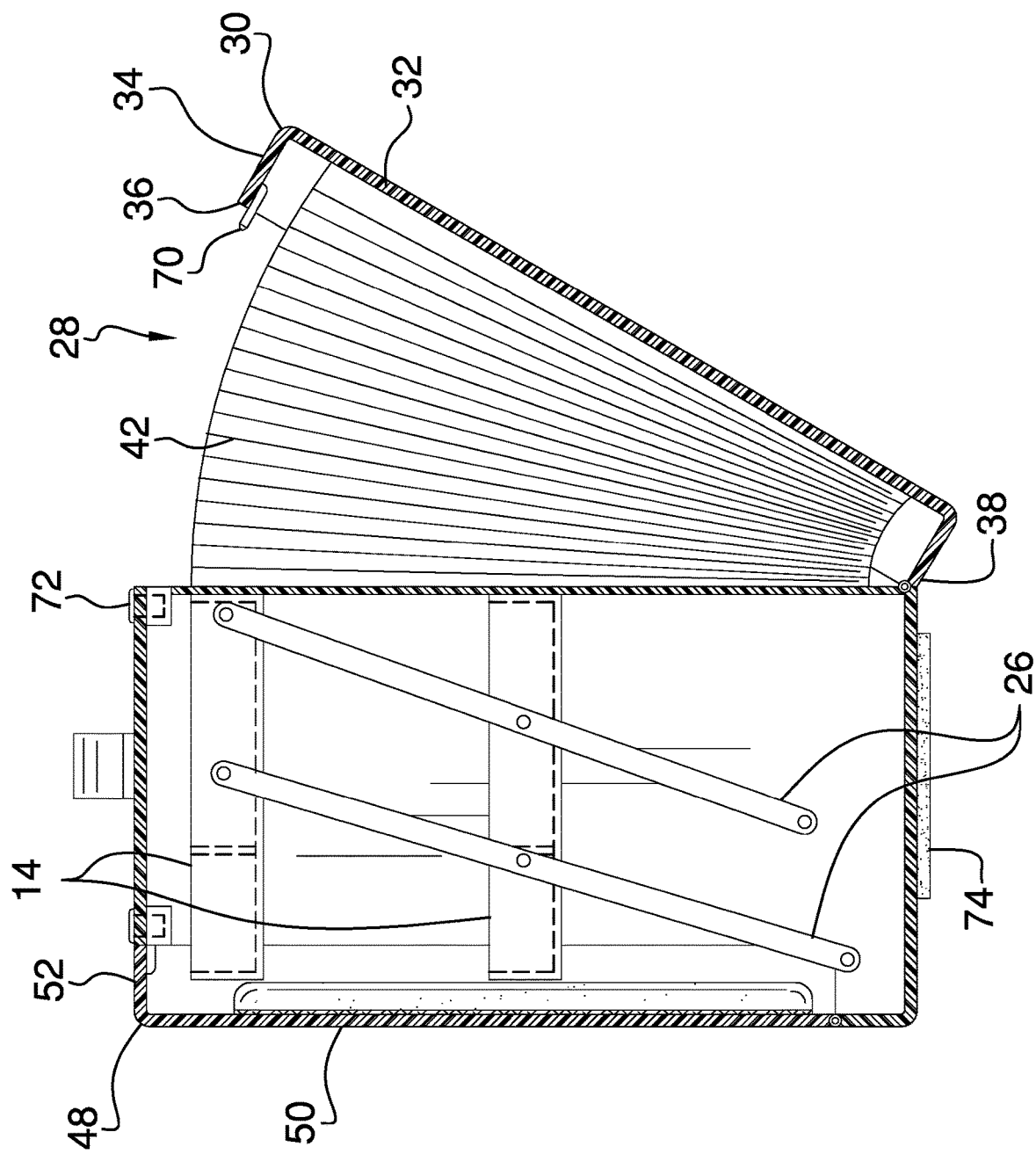
FIG. 5 is a right side cut-away view of an embodiment of the disclosure showing a file accordion being opened.
Figure 6:
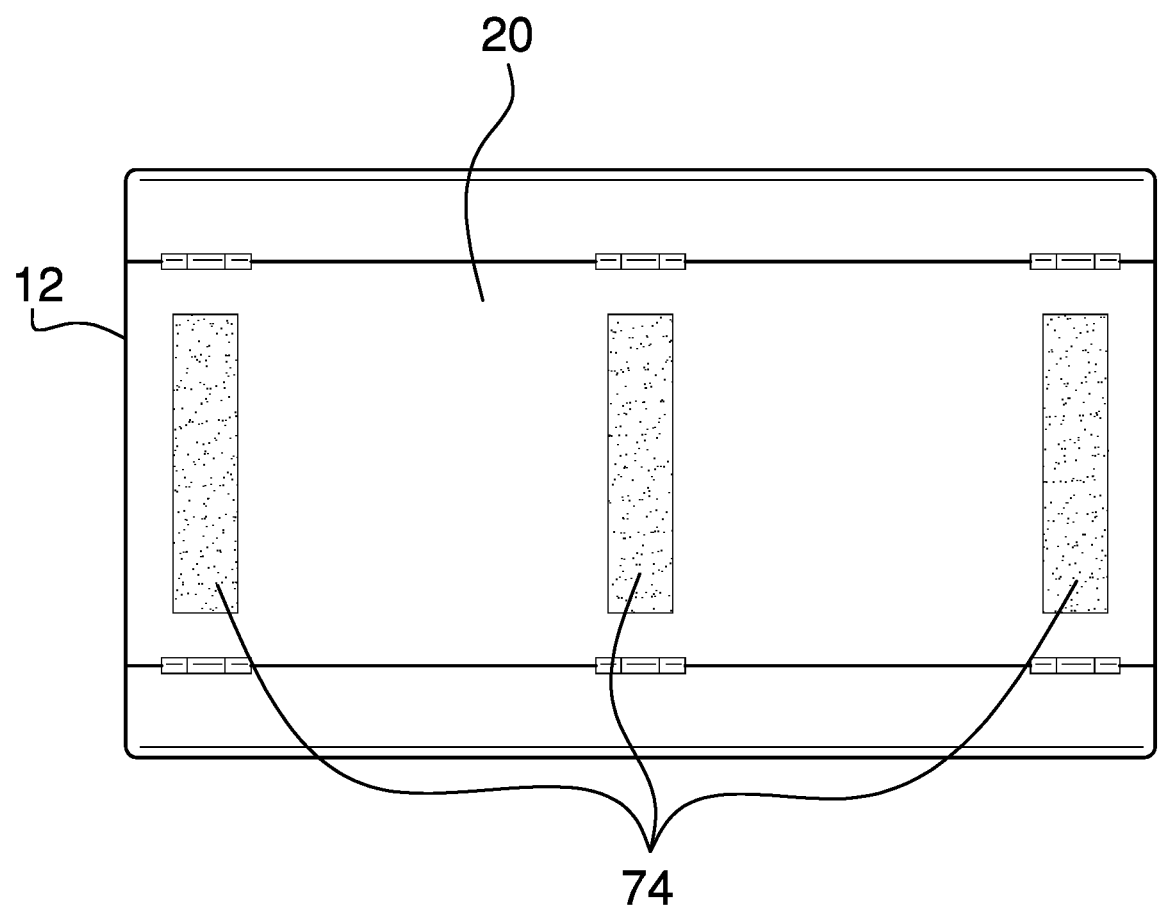
FIG. 6 is a bottom view of an embodiment of the disclosure.

With reference now to the drawings, and in particular to FIGS. 1 through 6 thereof, a new first aid device embodying the principles and concepts of an embodiment of the disclosure and generally designated by the reference numeral 10 will be described.

As best illustrated in FIGS. 1 through 6, the medical file and first aid assembly 10 generally comprises a storage case 12 that is carried by a trainer of a sports team, such as a football team, hockey team and any other organized sports team. The storage case 12 has a plurality of trays 14 that are each pivotally positioned therein for storing first aid supplies. The first aid supplies may be first aid supplies that are specific to treating sports injuries or the like.

The storage case 12 has a first end 16, a second end 18 and an outer wall 20 extending therebetween, the first end 16 is open to access an interior of the storage case 12, and the outer wall 20 has an inner surface 22 and an outer surface 24. The plurality of trays 14 includes a plurality of arms 26 and each of the arms 26 is pivotally coupled to the inner surface 22 of the outer wall 20. Each of the trays 14 is pivotally coupled between the arms 26 and each of the trays 14 is contained within the storage case 12 when the arms 26 are positioned in a stored position. Alternatively, each of the trays 14 extends outwardly through the first end 16 of the storage case 12 when the arms 26 are positioned in a deployed position. Thus, the trays 14 are positioned outside of the storage case 12 for accessing the first aid supplies that are contained in the trays 14.

A file accordion 28 is movably coupled to the storage case 12 for storing medical history of each player on the sports team. In that way the trainer has access to medical history of each player for safely applying first aid to each player. The file accordion 28 comprises a cover 30 that has a front wall 32 and a perimeter wall 34 extending rearwardly away therefrom. The perimeter wall 34 has a distal edge 36 with respect to the front wall 32, and a bottom side 38 of the distal edge 36 is hingedly coupled to the second end 18 of the storage case 12. Thus, a file space 40 is defined that extends between the second end 18 and the front wall 32 of the cover 30 for receiving the medical files. The distal edge 36 of the perimeter wall 34 abuts the second end 18 when the cover 30 is in a closed position and the distal edge 36 tilts away from the second end 18 when the cover 30 is in an open position.

A pair of pleated panels 42 is each coupled between the distal edge 36 of the perimeter wall 34 of the cover 30 and the second end 18 of the storage case 12 to partially surround the file space 40. In this way the pleated panels 42 retain the medical files in the file space 40 when the cover 30 is opened. The pair of pleated panels 42 extends along each of a first lateral side 44 and a second lateral side 46 of the distal edge 36. The pair of pleated panels 42 expands to extend between the distal edge 36 and the second end 18 when the cover 30 is in the open position. Alternatively, each of the pleated panels 42 is compressed between the distal edge 36 and the second end 18 when the cover 30 is in the closed position.

A door 48 is hingedly coupled to the storage case 12 for opening and closing the storage case 12. The door 48 has a forward wall 50 and a peripheral wall 52 extending rearwardly therefrom, and the peripheral wall 52 has a distal edge 54 with respect to the forward wall 50. The distal edge 54 of the peripheral wall 52 abuts the first end 16 of the storage case 12 when the door 48 is in a closed position to close the storage case 12. The distal edge 54 of the peripheral wall 52 tilts away from the first end 16 of the storage case 12 when the door 48 is in an open position, and the forward wall 50 has an inwardly facing surface 56.

A pad 60 is removably coupled to the door 48 and the pad 60 is positionable on a support surface thereby facilitating the trainer to kneel on the pad 60. Thus, the pad 60 enhances comfort for the trainer when the trainer is kneeling for delivering first aid or the like. A mating member 62 is coupled to the inwardly facing surface 56 of the forward wall 50 of the door 48. The pad 60 releasably engages the mating member 62 to retain the pad 60 on the door 48 for storage. The mating member 62 may be a hook and loop fastener or other type of fastener that can releasably engage the pad 60.

A communication unit 64 is provided and the communication unit 64 may be coupled to the door 48. The communication unit 64 may include a transceiver that is in wireless electrical communication with an extrinsic communication network, such as the internet, a cellular phone network and any other electronic communication network. Thus, inventory of the first aid supplies can be tracked and remotely ordered for re-supply via an app on a smart phone, a program on a personal computer and any other type of remote electronic communication. The communication unit 64 may comprise a smart tag or the like that functions accordion 28 to established inventory tracking and re-ordering protocols.

A first catch 66 is coupled to the door 48 and a first lock 68 is coupled to the outer wall 20 of the storage case 12. The first lock 68 is aligned with the first end 16 of the storage case 12 and the first lock 68 releasably engages the first catch 66 when the door 48 is in the closed position. A second catch 70 is coupled to the cover 30 and a second lock 72 is coupled to the outer wall 20 of the storage case 12. The second lock 72 is aligned with the second end 18 of the storage case 12 and the second lock 72 releasably engages the second catch 70 when the cover 30 is closed. Each of the first 68 and second 72 locks may be keyed locks or the like. A plurality of feet 74 is each coupled to a bottom side of the outer wall 20 of the storage case 12 for standing the storage case 12 on the feet 74.

In use, the medical files for each of the players on the sports team is positioned in the file accordion 28 and the first aid supplies are stored in the trays 14. The trainer carries the storage case 12 on the field of play during sport competition. Thus, the trainer has constant access to each player's medical history along with the first aid supplies. In this way the trainer can safely apply first aid to each player with respect to potential allergic reactions and other hazards with respect to applying first aid to the players. Additionally, the inventory of the first aid supplies can be tracked with the communication unit 64 and the first aid supplies can be remotely ordered for re-supply.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A medical file and first aid assembly being configured to store medical history of each individual on a team and first aid supplies, the assembly comprising:

a storage case being carried by a trainer of a sports team, the storage case having a plurality of trays being pivotally positioned therein for storing first aid supplies, the storage case has a first end, a second end and an outer wall extending therebetween, the first end being open to access an interior of the storage case, the outer wall having an inner surface and an outer surface, the plurality of trays including a plurality of arms, each of the arms being pivotally coupled to the inner surface of the outer wall, each of the trays being pivotally coupled between the arms, each of the trays being contained within the storage case when the arms are positioned in a stored position, each of the trays extending outwardly through the first end of the storage case when the arms are positioned in a deployed position;

a file accordion being movably coupled to the storage case for storing medical history of each player on the sports team wherein the file accordion is configured to facilitate the trainer to have access to medical history of each player for safely applying first aid to each player; and a communication unit being coupled to the storage case, the communication unit being in electrical communication with an extrinsic communication network thereby facilitating inventory of the first aid supplies to be tracked and remotely ordered for re-supply.

2. The assembly according to claim 1, wherein the file accordion comprises a cover having a front wall and a perimeter wall extending rearwardly away therefrom, the perimeter wall having a distal edge with respect to the front wall, a bottom side of the distal edge being hingedly coupled to the second end of the storage case to define a file space extending between the second end and the front wall of the cover for receiving the medical files, the distal edge of the perimeter wall abutting the second end when the cover is in a closed position, the distal edge tilting away from the second end when the cover is in an open position.

3. The assembly according to claim 2, further comprising a pair of pleated panels being coupled between the distal edge of the perimeter wall of the cover and the second end of the storage case to partially surround the file space thereby retaining the medical files in the file space when the cover is opened, the pair of pleated panels being extending along each of a first lateral side and a second lateral side of the distal edge, the pair of pleated panels expanding to extend between the distal edge and the second end when the cover is in the open position, the pair of pleated panels being compressed between the distal edge and the second end when the cover is in the closed position.

4. The assembly according to claim 2, further comprising:
a first catch;
a first lock;
a second catch being coupled to the cover; and
a second lock being coupled to the outer wall of the storage case, the second lock being aligned with the second end of the storage case, the second lock releasably engaging the second catch when the cover is closed.

5. The assembly according to claim 1, further comprising:
a door being hingedly coupled to the storage case for opening and closing the storage case, the door having a forward wall and a peripheral wall extending rearwardly therefrom, the peripheral wall having a distal edge with respect to the forward wall, the distal edge of the peripheral wall abutting the first end of the storage case when the door is in a closed position to close the storage case, the distal edge of the peripheral wall tilting away from the first end of the storage case when the door is in an open position, the forward wall having an inwardly facing surface;
a pad being removably coupled to the door, the pad being positionable on a support surface thereby facilitating the trainer to kneel on the pad wherein the pad is configured to enhance comfort for the trainer; and
a mating member being coupled to the inwardly facing surface of the forward wall of the door, the pad releasably engaging the mating member to retain the pad on the door for storage.

6. The assembly according to claim 5, further comprising:
a first catch being coupled to the door; and
a first lock being coupled to the outer wall of the storage case, the first lock being aligned with the first end of the storage case, the first lock releasably engaging the first catch when the door is in the closed position.

7. A medical file and first aid assembly being configured to store medical history of each individual on a team and first aid supplies, the assembly comprising:
a storage case being carried by a trainer of a sports team, the storage case having a plurality of trays being pivotally positioned therein for storing first aid supplies, the storage case having a first end, a second end and an outer wall extending therebetween, the first end being open to access an interior of the storage case, the outer wall having an inner surface and an outer surface, the plurality of trays including a plurality of arms, each of the arms being pivotally coupled to the inner surface of the outer wall, each of the trays being pivotally coupled between the arms, each of the trays being contained within the storage case when the arms are positioned in a stored position, each of the trays extending outwardly through the first end of the storage case when the arms are positioned in a deployed position;
a file accordion being movably coupled to the storage case for storing medical history of each player on the sports team wherein the file accordion is configured to facilitate the trainer to have access to medical history of each player for safely applying first aid to each player, the file according comprising:
  a cover having a front wall and a perimeter wall extending rearwardly away therefrom, the perimeter wall having a distal edge with respect to the front wall, a bottom side of the distal edge being hingedly coupled to the second end of the storage case to define a file space extending between the second end and the front wall of the cover for receiving the medical files, the distal edge of the perimeter wall abutting the second end when the cover is in a closed position, the distal edge tilting away from the second end when the cover is in an open position; and
  a pair of pleated panels being coupled between the distal edge of the perimeter wall of the cover and the second end of the storage case to partially surround the file space thereby retaining the medical files in the file space when the cover is opened, the pair of pleated panels being extending along each of a first lateral side and a second lateral side of the distal edge, the pair of pleated panels expanding to extend between the distal edge and the second end when the cover is in the open position, the pair of pleated panels being compressed between the distal edge and the second end when the cover is in the closed position;
a door being hingedly coupled to the storage case for opening and closing the storage case, the door having a forward wall and a peripheral wall extending rearwardly therefrom, the peripheral wall having a distal edge with respect to the forward wall, the distal edge of the peripheral wall abutting the first end of the storage case when the door is in a closed position to close the storage case, the distal edge of the peripheral wall tilting away from the first end of the storage case when the door is in an open position, the forward wall having an inwardly facing surface;
a pad being removably coupled to the door, the pad being positionable on a support surface thereby facilitating the trainer to kneel on the pad wherein the pad is configured to enhance comfort for the trainer;
a mating member being coupled to the inwardly facing surface of the forward wall of the door, the pad releasably engaging the mating member to retain the pad on the door for storage;
a communication unit being coupled to the storage case, the communication unit being in electrical communication with an extrinsic communication network thereby facilitating inventory of the first aid supplies to be tracked and remotely ordered for re-supply;
a first catch being coupled to the door;
a first lock being coupled to the outer wall of the storage case, the first lock being aligned with the first end of the storage case, the first lock releasably engaging the first catch when the door is in the closed position;
a second catch being coupled to the cover; and
a second lock being coupled to the outer wall of the storage case, the second lock being aligned with the second end of the storage case, the second lock releasably engaging the second catch when the cover is closed.

* * * * *